US00PP28077P3

(12) United States Plant Patent
Byrne et al.

(10) Patent No.: US PP28,077 P3
(45) Date of Patent: Jun. 6, 2017

(54) NECTARINE TREE NAMED 'SMOOTH DELIGHT ONE'

(50) Latin Name: *Prunus persica*
Varietal Denomination: Smooth Delight One

(71) Applicant: The Texas A&M University System, College Station, TX (US)

(72) Inventors: David H. Byrne, Bryan, TX (US); Natalie Anderson, Calvert, TX (US)

(73) Assignee: The Texas A&M University System, College Station, TX (US)

( * ) Notice: Subject to any disclaimer, the term of this patent is extended or adjusted under 35 U.S.C. 154(b) by 103 days.

(21) Appl. No.: 14/544,508

(22) Filed: Jan. 13, 2015

(65) Prior Publication Data

US 2016/0205824 P1 Jul. 14, 2016

(51) Int. Cl.
*A01H 5/08* (2006.01)

(52) U.S. Cl.
USPC ..... Plt./188

(58) Field of Classification Search
USPC ..... Plt./188
See application file for complete search history.

(56) References Cited

U.S. PATENT DOCUMENTS

PP9,332 P 10/1995 Zaiger et al.
PP9,871 P 4/1997 Sherman

OTHER PUBLICATIONS

The Brooks and Olmo Register of Fruit and Nut Varieties, 3rd Ed., American Society of Horticultural Science Press, Alexandria, VA, 1997.

Andrews et al.; 'FlordaKing' peach; HortScience; 1979; pp. 81-82; vol. 14.

Byrne et al.; 'TexRoyal', a Medium-chilling Peach; HortScience; Oct. 1991; pp. 1338-1340; vol. 26(10).

*Primary Examiner* — Keith Robinson
(74) *Attorney, Agent, or Firm* — Ramey & Schwaller, LLP

(57) ABSTRACT

Disclosed is a new variety of *Prunus persica* named 'Smooth Delight One'. This new variety, which requires 350-400 chilling units of dormancy, is considered to be a nectarine tree of early season maturity, ripens in early to mid-May in the medium chill zone of Texas, which produces white fleshed sub acid fruit that are very firm, attractively colored, and suitable for both local and regional markets.

4 Drawing Sheets

BACKGROUND OF THE INVENTION

Field of the Invention

This invention relates to nectarine trees and, more specifically, to nectarine trees referred to as a variety of *Prunus persica* named 'Smooth Delight One', which requires approximately 350 to 400 chilling units of dormancy, produces an high quality, firm clingstone sub-acid white fleshed nectarine that matures early in the season.

SUMMARY OF THE INVENTION

The 'Smooth Delight One' nectarine is characterized as to novelty and is otherwise noteworthy by producing a white nectarine that ripens in the early season; is considered good to high quality; and which is firm and has an attractive coloration. In this regard, the present variety of nectarine tree bears fruit that are ripe for commercial harvesting and shipment the second week of May when grow in south central Texas. 'Smooth Delight One' ripens 5-7 days after 'Flordaking' (not patented, Andrews et al., 1979) and about a week before 'TexKing' (U.S. Plant Pat. No. 14,627).

Origin of the Variety

The present nectarine tree was the result of an ongoing Stone Fruit Breeding Program of Texas A & M University, College Station, Brazos County, Tex. To this end, controlled crosses are made each year to produce seedling populations from which improved progenies are evaluated and selected.

The seedling 'TX2A232LWN' ('Smooth Delight One') was identified at the Texas A & M University Horticultural Farm in College Station, Tex. in 2003, and was chosen from a population of seedlings that resulted from seed from a cross between 'Sunmist' (U.S. Plant Pat. No. 9,871, Apr. 29, 1997) used as the female parent and 'Arctic Star' (U.S. Plant Pat. No. 9,332, Oct. 17, 1995) used as the male (pollen) parent. Resulting seed from this cross were planted at the Texas A & M University Horticultural Farm in College Station, Tex. 'TX2A232LWN' was marked for subsequent observation and noted as having exceptional characteristics. Two-year and older trees of the variety were subsequently evaluated during the 2005 through 2011 fruit growing seasons in both California (Fowler) and Texas (Floresville and College Station).

Asexual Reproduction of the Variety

'TX2A232LWN' was bud grafted onto virus-free Nemaguard (not patented, Brooks and Olmo, 1997) nectarine rootstock in June 2003 at the nursery site in Oakdale, Calif. The variety was subsequently planted at the experimental orchard in the central portion of the San Joaquin Valley, near Fowler, Fresno County, Calif. and in two sites in Texas (College Station and Floresville). Fruit from the resulting propagation has been evaluated during the period from 2005 to 2010 fruit seasons. This evaluation clearly demonstrated that the re-propagated trees were true to the characteristics of the original seedling in all observable aspects.

BRIEF DESCRIPTION OF THE DRAWINGS

This new variety of nectarine tree is illustrated by the accompanying photographs. The fruit, pits, flowers, and shoots depicted are from mature trees that are 5-years of age.

BOTANICAL DESCRIPTION OF THE VARIETY

Figure 1:
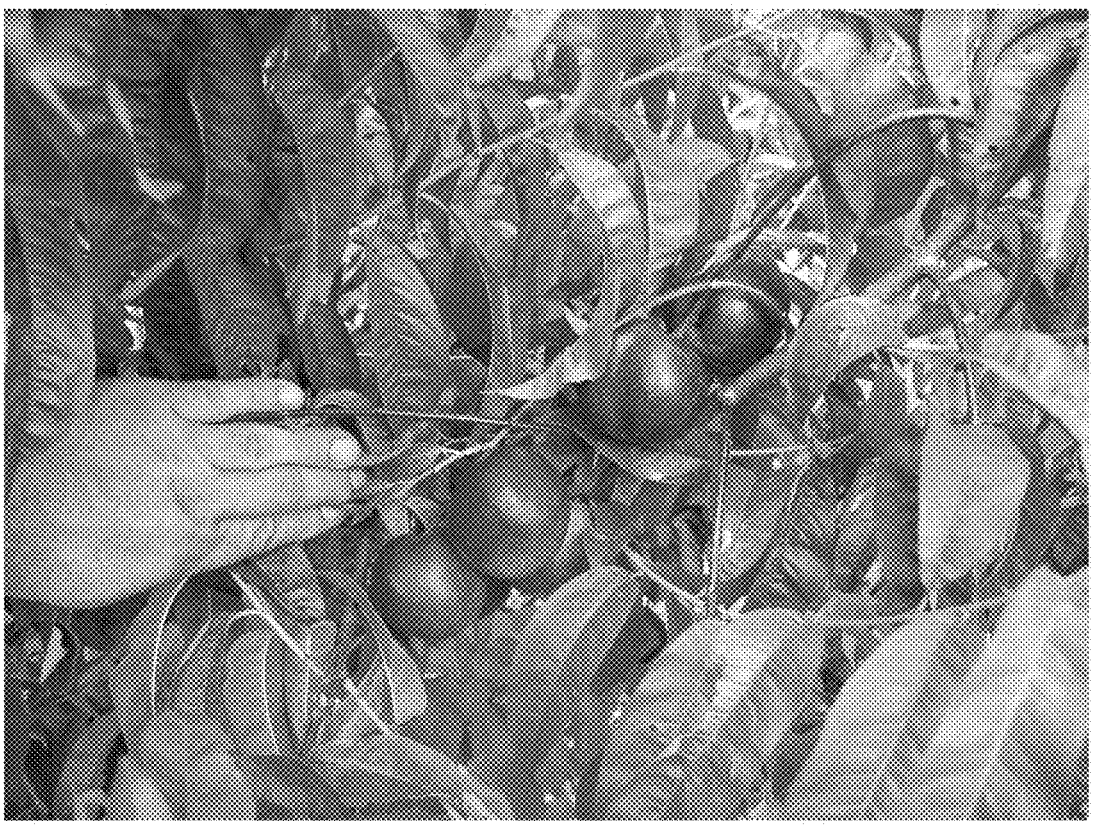
FIG. 1. 'Smooth Delight One' nectarine showing typical leaves and shoots.
Figure 2:
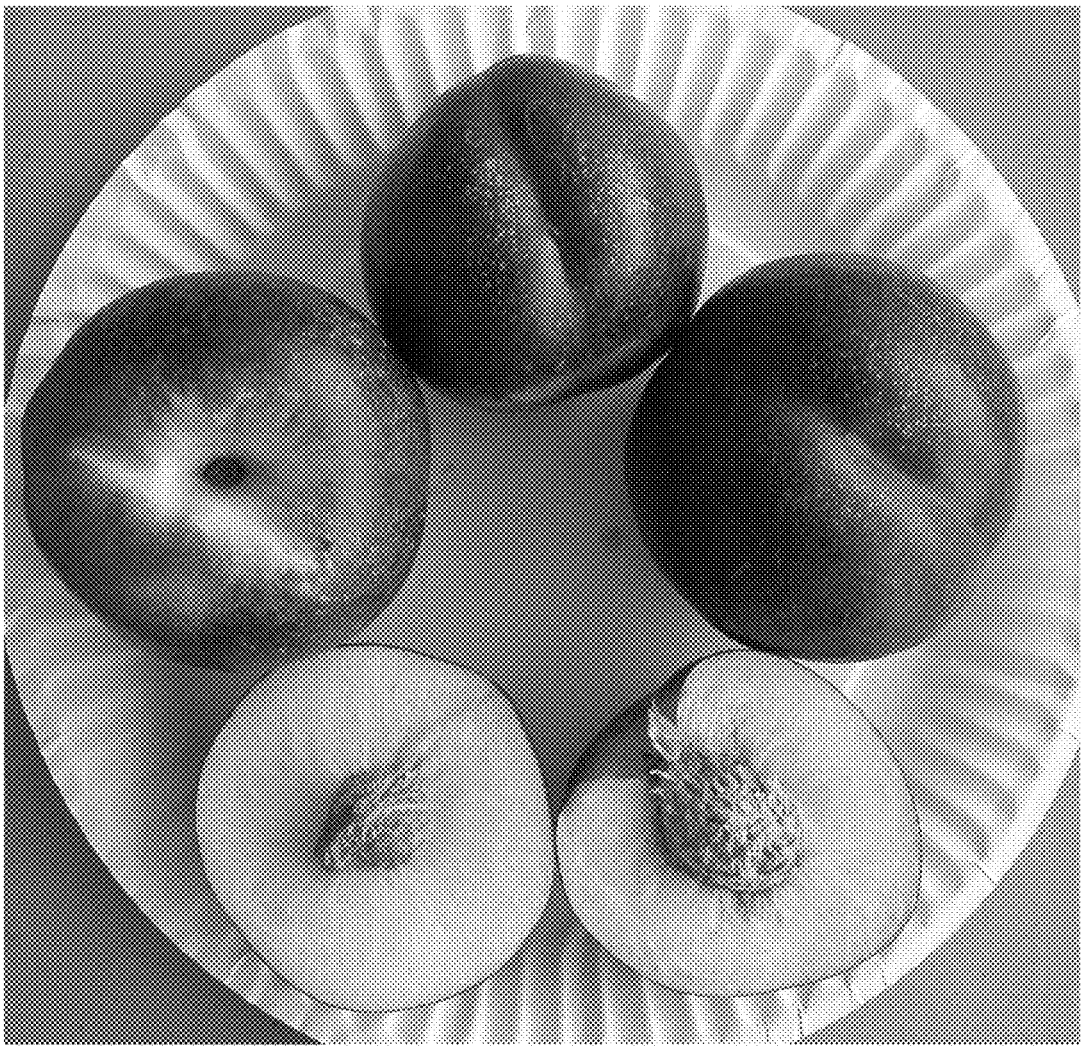
FIG. 2. Fruit of 'Smooth Delight One' produced in the evaluation blocks in Fowler, Calif. showing apical and distal views as well as fruit dissected in the axial or suture plane to illustrate the flesh, skin color, fruit shape and stone characteristics.
Figure 3:
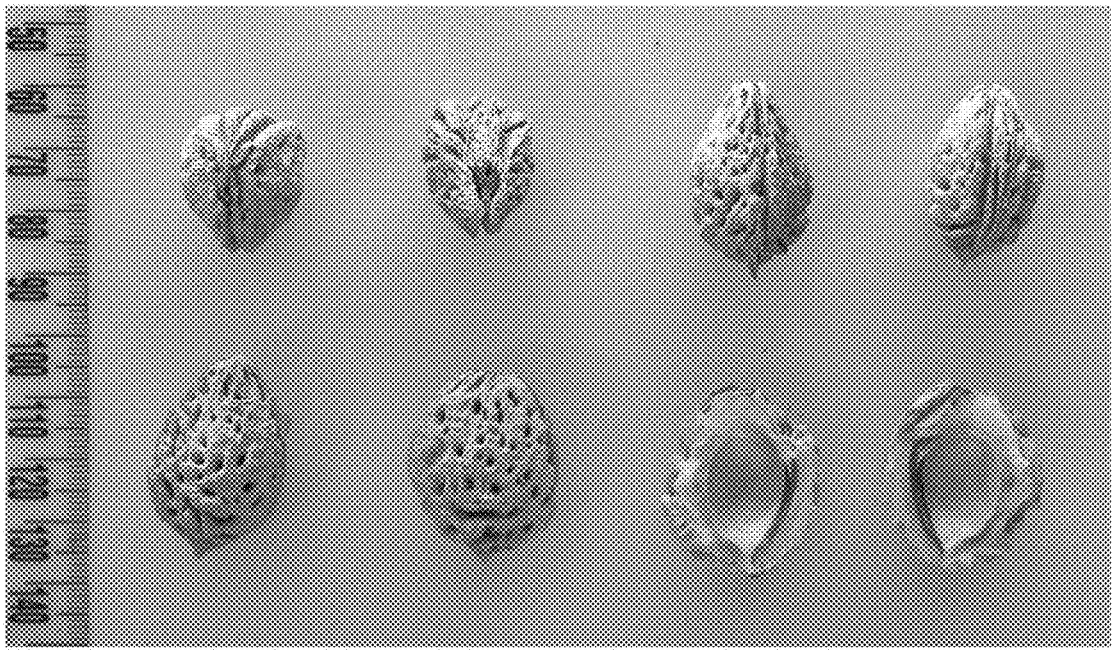
FIG. 3. Dried endocarps of 'Smooth Delight One' showing various views. The ruler is demarcated in millimeters.
Figure 4:
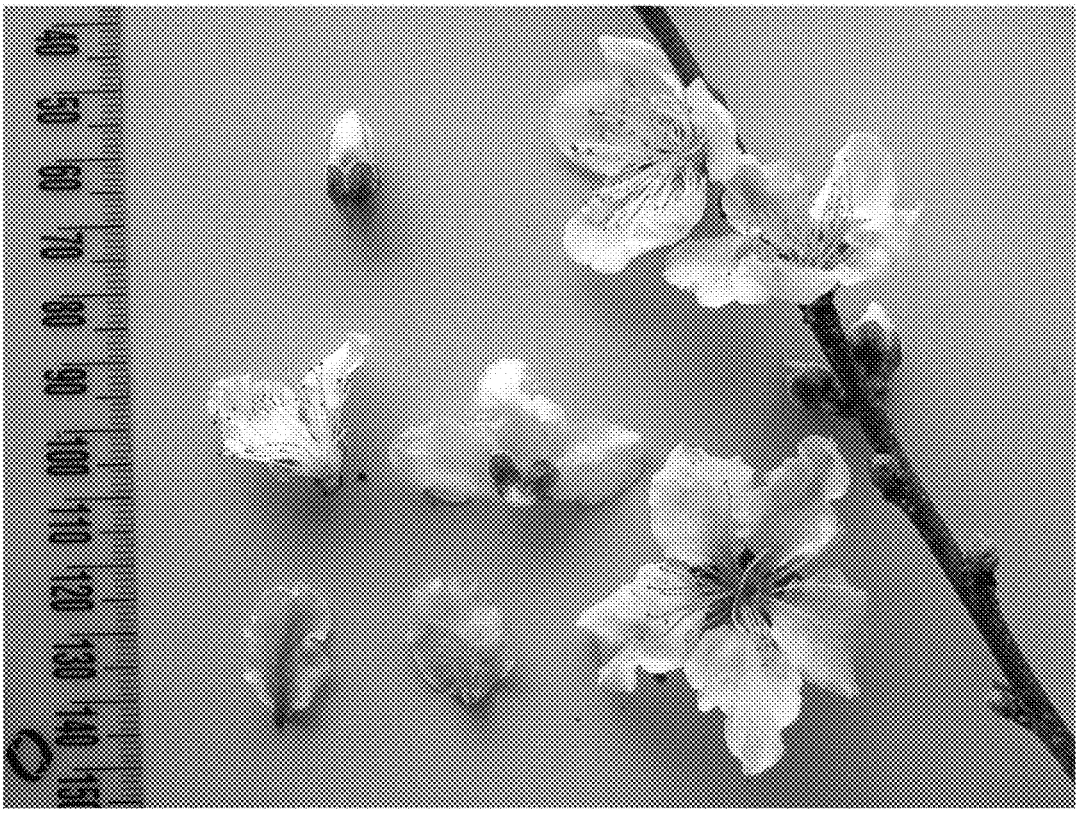
FIG. 4. The showy flowers of 'Smooth Delight One'. The ruler is in millimeters.

Referring more specifically to the pomological details of this new and distinct variety of nectarine tree, the following has been observed under the ecological conditions prevailing at the experimental orchards in the medium chill zone of Texas and in Fowler, Calif. on mature five-year old trees. All major color code designations are by reference to The R.H.S. Colour Chart (2001) provided by The Royal Horticultural Society of Great Britain. Colors are approximate as color depends on horticultural practices such as light level and fertilization rate, among others.

Tree

Size: Generally average to above average as compared to other common nectarine cultivars ripening in the early season of maturity.

Height: 10 feet (3.05 m) at the end of the 2012 growing season on a five-year old tree.

Width: 6 feet (1.83 m) at the end of the 2012 growing season on a five-year old tree.

Vigor: High.

Density: Medium to high.

Productivity: Productive.

Shape: The 'Smooth Delight One' exhibits a generally spreading growth habit typical of commercial varieties of nectarine such as 'TexKing' (U.S. Plant Pat. No. 14,627) and 'TexRoyal' (not patented, Byrne and Bacon, 1991).

Current season growth: The current season growth for the new variety was approximately 2.5 to 3.4 feet (0.76-1.04 m).

Regularity of bearing: Regular, and considered hardy under typical conditions in the medium chill zone of Texas and in the central San Joaquin Valley, Calif.

Trunk

Size: Approximately 4 inches (10.16 cm) in diameter and 12.5 inches (31.75 cm) in circumference when measured at a distance of approximately 12 inches (30.5 cm) above the soil level, at the end of the 2012 growing season on a five-year old tree.

Bark texture: Considered moderately rough with numerous folds of papery scarf-like skin being present.

Bark coloration: Variable, R.H.S. colors present are 200D and N200C-D of the Brown Group and 201C-D of the Grey Group.

Branches

Size: Considered medium for the variety. The length of the branches are limited by pruning to a 3 to 5 foot (approximately 0.9 to 1.5 m) depending on its position in the tree.

Thickness: Average (about 2.5 cm in diameter as measured 10 cm from the trunk on a five-year old tree) as compared to other varieties.

Surface texture: Average and appearing furrowed on wood that is several years old.

Lenticels: Numerous flat, oval lenticels present. The lenticels range in size from approximately 1 to 7 mm in width and were approximately 1-2 mm in height.

Current season shoots:

*Surface texture*.—Substantially glabrous.

Internode length: Approximately 15 to 24 mm as measured in the middle of a current season stem.

Color of mature branches: The predominant colors are 165A-B of the Greyed-Orange Group; 199A, N199C-D of the Grey-Brown Group; and 200D of the Brown Group.

Current season shoots:

*Color*.—Medium to light green (Green Group 140B, 141C-D, 142A-B and 143A-D and Yellow-Green Group 144A-C, N144C-145A and 146B-D) with some brown coloration appearing on exposed surface of the shoots (Grey-Brown Group 199A-B, and N199C-D). The upper exposed surface of current season growth exhibits medium intensity of anthocyanins.

Leaves

Size: Considered moderately small for the species. Leaf measurements have been taken from vigorous upright current season growth approximately at mid-shoot.

Leaf length: Approximately 126 to 149 mm.

Leaf width: Approximately 36 to 44 mm.

Leaf thickness: Less than 1 mm.

Leaf form: Lanceolate.

Leaf tip form: Acuminate.

Leaf upper surface color: Green varying among 137A-C of the Green Group and 146A-C of the Yellow Green Group.

Leaf lower surface color: Green varying among 138B of the Green Group and 146A-D of the Yellow-Green Group.

Leaf mid-vein color: Light yellow green (145C-D of the Yellow-Green Group and 160D of the Greyed-Yellow Group).

Leaf margins:

*Form*.—Considered crenulate.

*Uniformity*.—Considered generally uniform.

Leaf petioles:

*Size*.—Considered medium long.

*Length*.—Approximately 9 to 11 mm.

*Thickness*.—Approximately less than 1 mm.

*Color*.—Pale green (Yellow Green Group 144C and N144C-D).

Leaf glands:

*Size*.—Approximately 1 mm in height and 1 to 1.5 mm in width.

*Number*.—Generally 2-4 per leaf.

*Type*.—Reniform.

*Color*.—Greenish brown (199A-D and N199A-D of the Grey-Brown Group).

Leaf stipules:

*Size*.—Considered medium to large for the species.

*Length*.—Approximately 10-16 mm.

*Width*.—Approximately 1 mm.

*Form*.—Lanceolate.

*Color*.—Light green (RHS Yellow-Green 144B-D and N144C-D). The stipules are considered early deciduous.

*Ratio of wood (leaf) buds to flowering buds*.—1 to 2 flower buds per vegetative bud.

Flowers

Floral buds:

*General*.—The floral buds are considered to be medium large to large in size, conic in form, and slightly appressed relative to the bearing shoot.

*Color*.—The bud scales are brown with a greenish white color, (approximately Red-Purple Group 58A, Green-White Group 157A-B and the Brown Group 200A-D). The buds are considered hardy under typical environmental conditions in the medium and low chill zones of Texas and in the central San Joaquin Valley, Calif.

*Length*.—Approximately 6 to 10 mm.

*Width*.—Appoximately 2-3 mm.

*Blooming type*.—It bloomed in mid to late February in Floresville, Tex. and Fowler, Calif. respectively. It bloomed slightly before or with common medium chill cultivars such as 'Flordaking' (not patented, Andrews et al., 1979), TexKing' (U.S. Plant Pat. No. 14,627), and 'Sunraycer' (not patented, Sherman and Lyrene, 1995). It is estimated to require between 350 and 400 chilling units to break winter dormancy.

*Flower type*.—Showy.

*Flower size*.—Flower diameter at full bloom is approximately 38 to 45 mm. The length of the flower at the pink bud stage before opening ranges from 12 to 18 mm.

*Bloom quantity*.—Considered abundant.

*Flower bud frequency*.—Normally 1 to 2 per node.

Petal size:

*General*.—Considered medium large for the species.

*Width*.—Approximately 14 to 17 mm.

*Length*.—Approximately 19 to 20 mm.

*Petal form*.—Broadly ovate.

*Petal count*.—Nearly always 5.

*Petal color*.—Medium to dark pink when young (Red Group 54A-55D, Red-Purple Group N57A-58C, 61C-63D, 65A-B and N66B-D), becoming darker near the petal claw. As petals age, color becomes darker pink (Red Group 56A, Red-Purple Group 58D, 64D, 65A-D, 68C-69C, 70D and Purple Group 75B-D).

Petal claw:

*Form*.—The claw is considered present.

*Length*.—Approximately 1 to 1.5 mm.

*Width*.—Approximately 1 to 1.5 mm.

*Petal margins*.—Generally considered variable, from nearly smooth to slightly undulate.

*Petal apex*.—Generally — The petal apices appear slightly domed and rounded.

Flower pedicel:

*Length*.—Considered medium to long, and having an average length of approximately 4 to 5 mm.

*Thickness*.—Considered average, approximately 1 to 1.5 mm.

*Color*.—A light green (Yellow-Green Group 145A-B and N144B-D).

Floral nectaries:

*Color*.—Dull yellow (Yellow-Green Group 153A-D).

Calyx:

*Surface texture*.—Generally glabrous.

*Color*.—Green (approximately Yellow-Green Group 144C, N144D, 145A-C and 149A-151D) with maroon (Red-Purple Group 59A-60A), red (Red Group 46A-B, 47A-B and 53A-B) and brown (Greyed-Orange Group 165A, 166A-B, 174A and 175A-B).

Sepals:

*Surface texture*.—The surface has a short, fine, and wooly texture.

*Size*.—Average, and ovate in form. Sepal lengths range from 5.5 to 6.0 mm and the width from 4.4 to 4.8 mm at the pink bud to open flower states of development.

*Color*.—All colors represented in Calyx color plus an additional green (approximately Greyed-Green Groups 190-194A-D).

Anthers:

*General*.—Average in size for the species. Anther length ranges from 1.5 to 2.0 mm and the width was approximately 1 mm.

*Color*.—Yellow (approximately Green-Yellow Group 1A-B, Yellow Group 2A-7A) and darkening upon aging.

*Pollen production*.—Pollen is abundant, and is a yellow color (approximately Yellow Group 7A-13A).

Filaments:

*Size*.—Variable in length, approximately 14 to 16 mm, with the filaments slightly longer than the pistil. The stamens are generally higher than the pistil and do not protrude when the flowers are at the pink bud stage of development.

*Color*.—White with pink tinge (approximately White Group 155A-D and N155A-D; RHS Orange Group 27D, Red Group 36D and 49D) and darkening with advanced maturity.

Pistil:

*General*.—Average in size, but slightly shorter, relative to the general stamen height, overall. The anthers are above the pistil.

*Length*.—Approximately 14 to 16.5 mm, including the ovary.

*Color*.—Considered a greenish-yellow when young (approximately Yellow-Green Group 144C, N144B, 149B-151B and 154A), and becoming slightly darker with advancing senescence.

*Surface texture*.—The pistil including the ovary is glabrous and is not pubescent.

Fruit

Maturity when described: The present variety of fruit is described, as it would be found in its firm ripe condition at full commercial maturity. Under the ecological conditions prevailing in the medium chill zone of Texas 'Smooth Delight One' ripens in early to mid May, 4-5 days after 'Flordaking' (not patented, Andrews et al., 1979) and about a week before 'TexKing' (U.S. Plant Pat. No. 14,627).

Size:

*General*.—Medium large to large for the season and considered uniform.

*Average cheek diameter*.—Approximately 64 to 71 mm.

*Average suture diameter*.—Approximately 63 to 73 mm.

*Average axial diameter*.—Approximately 63 to 69 mm.

Fruit form: Generally round in its lateral aspect. The fruit is generally uniform in symmetry when viewed from the apical aspect.

Fruit suture: Generally, the suture appears as a thin line that extends from the base to the apex, and appears deeper at the apex, forming a shallow basin at the apical point. No apparent callusing or stitching exists along the suture line.

*Color*.—The suture normally is darker than the underlying blush. RHS Red Group 53A-B and Red Group 46A-B.

*Ventral surface*.—Form — Considered uniform.

Stem cavity:

*Size*.—Considered moderately shallow for the species.

*Length*.—Approximately 13 to 16 mm.

*Width*.—Approximately 19 to 21 mm.

*Depth*.—Approximately 9 to 10 mm.

*Fruit base*.—Flat and tapering.

*Fruit apex*.—Flat.

Fruit stem:

*Length*.—Approximately 9 to 11 mm.

*Thickness*.—Approximately 2 to 3 mm.

*Color*.—Generally light green in color (Yellow-Green Group 144A).

Fruit skin: Generally considered medium or average in thickness.

*Surface texture*.—Smooth.

*Skin acidity*.—Considered neutral.

*Tenacious to flesh*.—Yes at commercial maturity.

*Tendency to crack*.—Generally resistant to cracking as compared to other varieties.

*Skin color*.—Generally — Variable, with a high (70%) to very high (90%) percentage of the fruit surface covered with blush as described under Blush Color below.

*Pubescence*.—Absent. The glabrous skin has medium glossiness.

*Blush color*.—It ranges from a light red (RHS Red Group 39A) to a dark red (RHS Red-Purple Group 59A-B and Greyed-Purple Group 183A-C) with many degrees of shading and blending occurring between these colorations.

*Skin ground color*.—This is generally present in variable percentages covering approximately 70-90% of the fruit's surface. The skin ground color is a greenish yellow (RHS Green-Yellow group 1B-D and Greyed-Yellow group 160B).

*Flesh color*.—Generally considered variable from a white coloration (White Groups 155B and N999D) to a very light pink (White Group N155B) with red appearing closer to the outer skin (Greyed-Purple Group 186A-D).

*Flesh fibers*.—Present, numerous and lightly colored. These fibers are present throughout the flesh.

*Stone cavity color*.—Generally considered white in color (White Group 155B).

*Flesh texture*.—Generally, the flesh is considered firm at commercial maturity.

*Ripening*.—Generally the fruit of the present variety ripens evenly.

*Flavor*.—Considered very sweet with sub acid flavor.

*Aroma*.—Pleasant and reasonably abundant.

*Eating*.—Generally considered good to excellent, particularly for its ripening season.

Stone

Attachment: Clingstone (strongly adherent) at commercial maturity.

Stone size: Generally considered medium to medium-large relative to the ratio of stone to fruit size.

*Length*.—Approximately 30 to 34 mm.

*Width*.—Approximately 22 to 24 mm.

*Thickness*.—Approximately 17 to 20 mm.

Stone form: Generally, the stone is considered elliptical to ovate.

Stone base: Narrow to medium.

Base angle: The base angle of the stone is variable, but most frequently is considered wide.

Apex shape: Narrow.

Stone shape: Considered variable, from ovoid to elongated.

Stone surface:

*Surface texture*.—Minor surface markings are honeycombed with some single pits and rosettes of pits.

*Ridges*.—Ridges are present basally, and converge towards the base of the stone.

*Ventral edge*.—Considered small.

*Dorsal edge*.—Shape — Grooved and having moderately rough edges.

*Stone color*.—The color of the dry stone is light brown (similar to Greyed-Orange Group 164C and 165D). The color of the inside surface of the endocarp is primarily Greyed-Orange Group 164C-D and 165C-D.

*Tendency to split*.—Splitting is uncommon.

*Kernel*.—The kernel fills the endocarp at harvest and measures approximately 6 mm in thickness, 9-10 m in width, and 15-17 mm in length. When dried the shriveled kernels measure approximately 1.5-3 mm in thickness, 7-9 mm in width, and 14-16 mm in length. The colors of the shriveled kernels are primarily Greyed-Yellow Group 161C-D and Greyed-Orange Group 164C-D.

Use: The subject variety, 'Smooth Delight One', is considered to be a nectarine tree of early season maturity, which produces white fleshed fruit which are firm, attractively colored, sub acid in flavor and which are useful for both local and regional markets.

Keeping quality: Good.

Resistance to insects and disease: No particular susceptibilities or resistances were noted or are claimed.

Shipping quality: Average.

Although the new variety of nectarine tree possesses the described characteristics when grown under the ecological conditions prevailing in the medium chill zone of Texas and in Fowler, Fresno County, Calif., it will be understood that variations of the usual magnitude and characteristics incident to the changes in growing conditions, fertilization, pruning, and pest control are to be expected.

LITERATURE:

Andrews, C. P., W. B. Sherman, and P. M. Lyrene. 1979. 'Flordaking' peach. HortScience 14:81-82.

Anon. 2001. R.H.S. Colour Chart. The Royal Hort. Soc., London.

Brooks, R. M. and H. P. Olmo. 1997. Register of New Fruit and Nut Varieties. 3rd Edition. American Society of Horticultural Science Press, Alexandria, Va.

Byrne, D. H. and T. A. Bacon. 1991. 'TexRoyal', a medium chilling peach. HortScience 26(10):1338-1340.

Byrne, D. H. and T. A. Bacon. 2004. 'TexKing', an early ripening medium chill peach. HortScience 39: 442-443. U.S. Plant Pat. No. 14,627. Mar. 23, 2004.

Sherman, W. B. 1997. Nectarine tree called "Sunmist". U.S. Plant Pat. No. 9,871. Apr. 29, 1997.

Sherman, W. B., P. C. Andersen, and P. M. Lyrene. 1995. 'Sunmist' nectarine. HortScience 30(1): 155.

Sherman, W. B., P. C. Andersen, and P. M. Lyrene. 1995. 'Sunraycer' nectarine. HortScience 30(1): 154.

Zaiger, C., G. Zaiger, L. M. Gardner, and G. Zaiger. 1994. Nectarine tree "Arctic Star". U.S. Plant Pat. No. 9,332, Oct. 17, 1995.

We claim:

1. A new and distinct *Prunus persica* tree, substantially as illustrated and described herein.

* * * * *